US00PP28954P2

(12) United States Plant Patent
Thompson

(10) Patent No.: US PP28,954 P2
(45) Date of Patent: Feb. 13, 2018

(54) JAPANESE HASKAP PLANT NAMED 'PIRIKA'

(50) Latin Name: *Lonicera caerulea var. emphyllocalyx*
Varietal Denomination: Pirika

(71) Applicant: Maxine M. Thompson, Corvallis, OR (US)

(72) Inventor: Maxine M. Thompson, Corvallis, OR (US)

(73) Assignee: MAXINE M. THOMPSON TRUST, Corvallis, OR (US)

( * ) Notice: Subject to any disclaimer, the term of this patent is extended or adjusted under 35 U.S.C. 154(b) by 0 days.

(21) Appl. No.: 15/330,323

(22) Filed: Sep. 6, 2016

(51) Int. Cl.
*A01H 5/08* (2006.01)

(52) U.S. Cl.
USPC ..... Plt./156

(58) Field of Classification Search
USPC ..... Plt./156, 226
CPC ..... A01H 5/08; A01H 5/02; A01H 5/00
See application file for complete search history.

*Primary Examiner* — June Hwu
(74) *Attorney, Agent, or Firm* — Penny J. Aguirre

(57) ABSTRACT

A new cultivar of Japanese haskap plant named 'Pirika' that is characterized by its upright and spreading plant habit, its vigorous and somewhat open branching habit, its above average fruit yields, its fruits that are attractive in appearance and elliptical in shape with some having rolled edges to appear jug-shaped its fruits that are large in size, its fruit that maintain their appearance, firmness and taste for at least 2 weeks in cold storage, its pleasant, mild tasting fruits with a BRIX of 14° and its fruit attachment to the peduncle that is strong enough to prevent pre-harvest drop, yet loose enough to permit picking without tearing the fruit flesh.

2 Drawing Sheets

Botanical classification: *Lonicera caerulea* var. *emphyllocalyx*.

Variety denomination: 'Pirika'.

CROSS REFERENCE TO RELATED APPLICATIONS

This application is co-pending with a U.S. Plant Patent Application filed derived from the same breeding program that is entitled Japanese haskap Plant Named 'Kapu' (U.S. Plant Pat. No. 26,820) and Japanese haskap Plant Named 'Kaido' (U.S. Plant patent application Ser. No. 14/757,025).

BACKGROUND OF THE INVENTION

The present invention relates to a new and distinct cultivar of *Lonicera caerulea* ssp. *emphyllocalyx* and will be referred to hereafter by its cultivar name, 'Pirika'. 'Pirika' is a new cultivar of Japanese blue honeysuckle berry, also known as Japanese haskap, a plant grown for its fruit that is marketed as fresh and frozen fruit and processed food products.

The new Invention arose from an ongoing controlled breeding program in Corvallis, Oreg. with the planting of seeds collected in 2000 from several berry farms in Hokkaido, Japan. The objectives of the breeding program are to develop superior cultivars of this early ripening berry plant that could be grown in moderate to colder climates combined with an upright spreading plant habit and fruit that are large in size, attractive in appearance, firm texture, easy to pick, pleasant taste, a high yield rate, easy to pick berries with a medium to strong attachment to the berry peduncle and a range of fruit maturity spreading throughout the harvest season.

This new cultivar, 'Pirika', arose from a controlled cross made in 2004 between unnamed and unpatented proprietary seedlings from the Inventor's breeding program; selection No. 21-20 as the female parent and selection No. 21-78 as the male parent. The Inventor selected 'Pirika' in 2008 as a single unique plant from amongst the seedlings that resulted from the above cross.

Asexual propagation of the new cultivar was first accomplished by the Inventor by hardwood stem cuttings in 2008 in Corvallis, Oreg. Asexual propagation by hardwood and softwood cuttings has determined that the characteristics of the new cultivar are stable and are reproduced true to type in successive generations.

SUMMARY OF THE INVENTION

The following traits have been repeatedly observed and represent the characteristics of the new cultivar as grown outdoors in a trial plot for eight years in Corvallis, Oreg. These attributes in combination distinguish 'Pirika' as a unique cultivar of Japanese haskap.

1. 'Pirika' exhibits an upright and spreading plant habit.
2. 'Pirika' exhibits a vigorous and somewhat open branching habit.
3. 'Pirika' exhibits above average fruit yields.
4. 'Pirika' exhibits fruit that are attractive in appearance and elliptical in shape with some having rolled edges to appear jug-shaped.
5. 'Pirika' exhibits fruit that are large in size.
6. 'Pirika' exhibits fruit that maintain their appearance, firmness and taste for at least 2 weeks in cold storage.
7. 'Pirika' exhibits pleasant, mild tasting fruits with a BRIX of 14°.
8. 'Pirika' exhibits fruit attachment to the peduncle that is strong enough to prevent pre-harvest drop, yet loose enough to permit picking without tearing the fruit flesh.

The female parent differs from 'Pirika' in having fruit that is smaller in size with a softer texture and a flavor that is more tart. The male parent differs from 'Pirika' in having fruit that is much smaller in size and that have a weaker attachment to the peduncle causing considerable pre-harvest drop. 'Pirika' can be most closely compared to the cultivar 'Kapu' and 'Kaido'. 'Kapu' differs from 'Pirika' in having fruit that is much firmer and smaller in size and in having a more upright plant habit. 'Kaido' differs from 'Pirika' in having a less vigorous growth habit, a smaller plant size, and fruit that is smaller in size and cylindrical in shape.

BRIEF DESCRIPTION OF THE DRAWINGS

The accompanying colored photographs were taken of 4 year-old plants in a research garden plot in Corvallis, Oreg.

The photograph in FIG. 1 provides a view of the plant habit of 'Pirika'.

Figure 1:
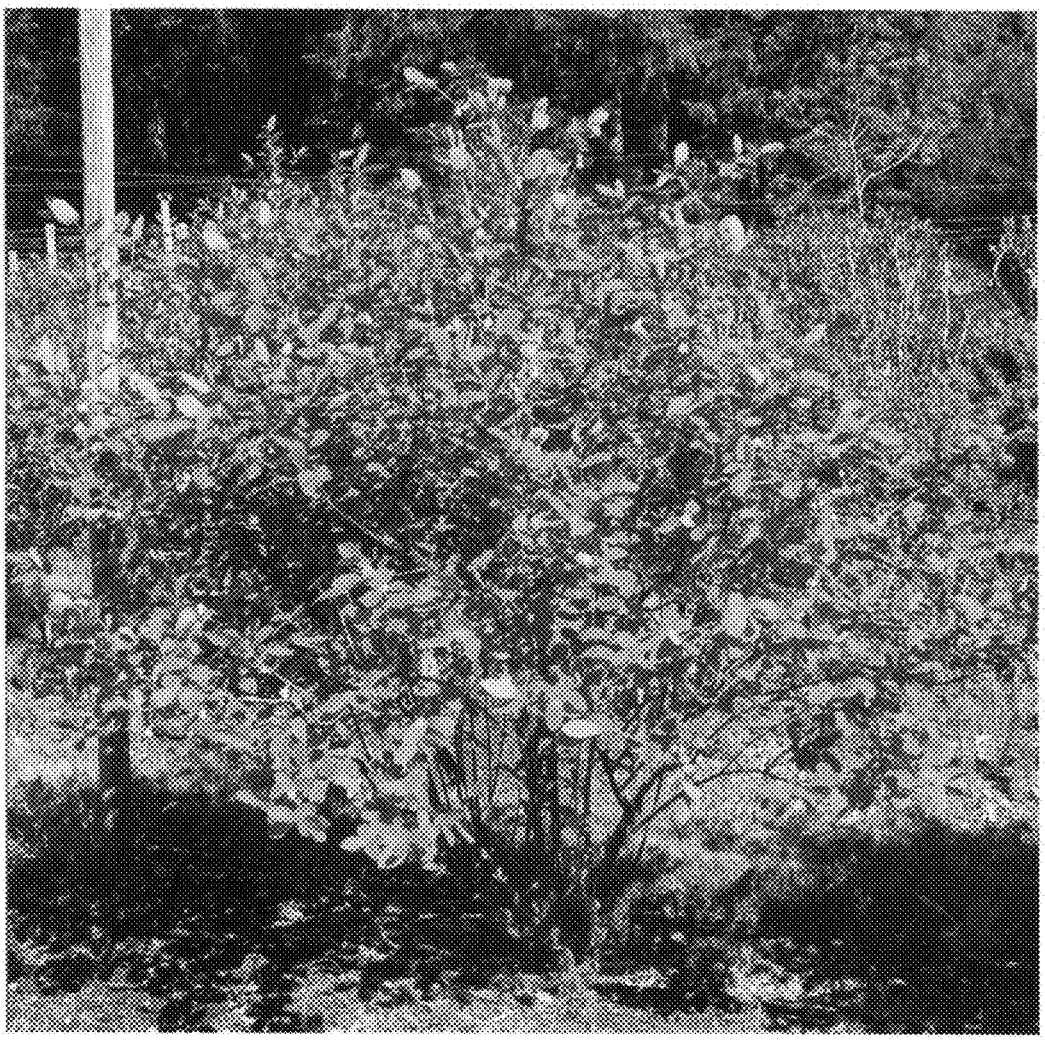
Figure 2:
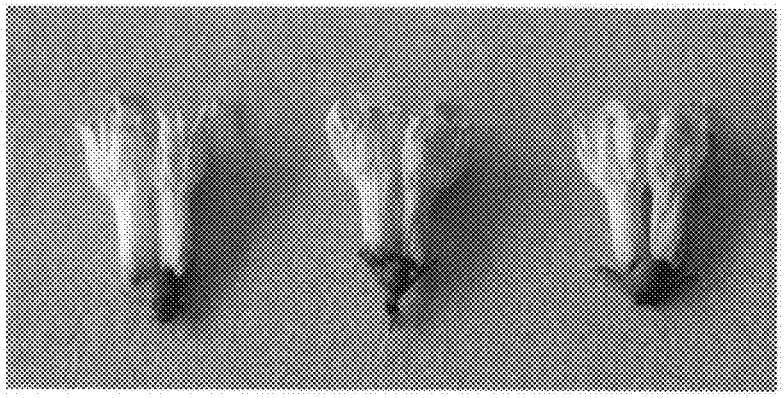

The photograph in FIG. 2 provides a close-up view of the flowers of 'Pirika'.

Figure 3:
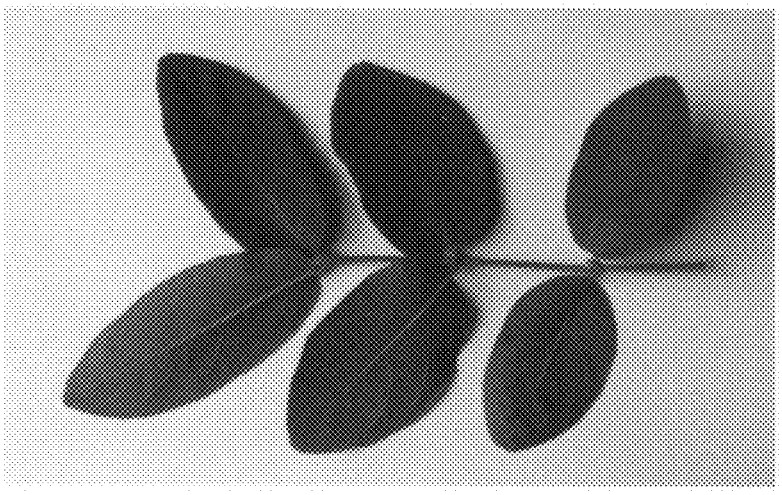

The photograph in FIG. 3 provides a close-up view of the leaves of 'Pirika'.

Figure 4:
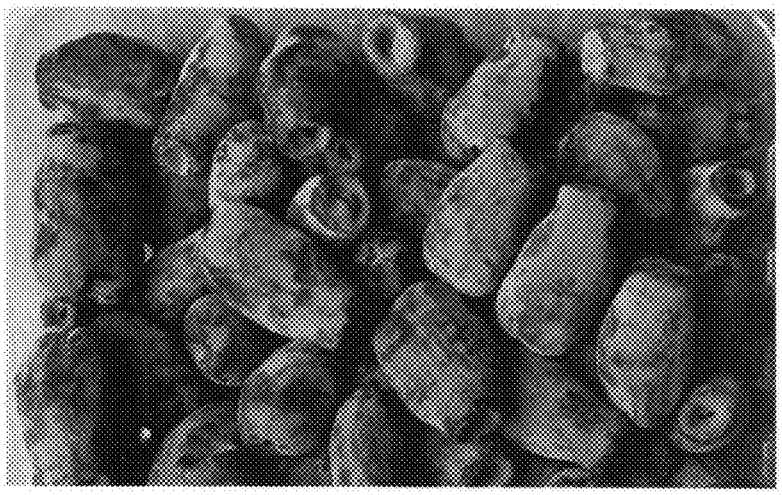

The photograph in FIG. 4 provides a view of the fruit of 'Pirika'.

The colors in the photographs may differ slightly from the color values cited in the detailed botanical description, which accurately describe the colors of the new haskap.

DETAILED BOTANICAL DESCRIPTION

The following is a detailed description of 7 year-old plants of the new Japanese haskap as grown outdoors on the Inventor's research plot in Corvallis, Oreg. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type*.—Deciduous shrub, fruit bearing.

*Plant habit*.—Upright and spreading.

*Plant size*.—Up to 1.8 m in height and 1.5 m in width.

*Hardiness*.—At least hardy to U.S.D.A. Zones 4 to 8.

*Diseases and pests*.—No pests or disease problems have been observed.

*Root description*.—Fibrous.

*Propagation*.—Softwood and hardwood stem cuttings.

*Root development*.—Dormant cuttings stuck outside in early March are transplanted as rooted cuttings into 4×4×9 inch tubes in early May; when transplanted in the ground, plants reach 30.5 cm to 46 cm in height by fall.

*Growth rate*.—Highly vigorous.

Dormant shoots:

*Density*.—Medium.

*New growth*.—137D in color, glabrous surface.

*One year-old shoots*.—Average of 33 cm in length and 5 mm in diameter, surface is smooth and glabrous, 200D in color.

*Three year-old shoots*.—75 cm in length, 1.5 cm in diameter, surface exfoliating with inner bark 170B in color and outer bark 200D in color.

Foliage description:

*Leaf shape*.—Elliptic.

*Leaf division*.—Simple.

*Leaf base*.—Round.

*Leaf apex*.—Obtuse.

*Leaf venation*.—Pinnate, color primarily matches leaf color on both surfaces.

*Leaf margins*.—Entire, setulose.

*Leaf arrangement*.—Opposite.

*Leaf attachment*.—Petiolate.

*Leaf surface*.—Young and mature leaf upper and lower surface; glabrous.

*Leaf internode length*.—3 to 4 cm.

*Leaf size*.—6 to 7 cm in length and 3 to 4 cm in width.

*Leaf color*.—Young leaves upper surface; 138A, young leaves lower surface; 138B, mature leaves upper surface; 137A, mature leaves lower surface; 138A.

*Petioles*.—1 mm in length and width, 145B in color, glabrous surface, moderately strong.

*Stipules*.—Absent.

Inflorescence description:

*Blooming period*.—March 29$^{th}$ to April 15$^{th}$ in Corvallis, Oreg. (average over 4 years).

*Inflorescence type*.—Small 2-flowered cymule born in leaf axils of lowest 1 to 4 nodes on current years shoot.

*Inflorescence size*.—An average of 2 cm in length and diameter.

*Flower buds*.—Mixed buds; flower buds are not visible as they are enclosed within the leaves of the bud.

*Flower fragrance*.—None.

*Lastingness of inflorescence*.—An average of 4 to 6 days.

*Flower type*.—Epigynous.

*Corolla form*.—Funnel-form, narrow at base, widening towards the apex, 5-lobed.

*Flower size*.—2.2 cm in length from base of ovary to tip of stigma, 10 mm in width at widest part.

*Flower number*.—An average of 2 to 6 flowers per shoot.

*Peduncles*.—2 mm in length, 1 mm in diameter, 135C in color, glabrous surface, moderately strong.

*Pedicels*.—Inconspicuous.

*Bracts*.—2, present at base of ovaries, linear in shape, color 135C on upper and lower surface, both surfaces glabrous, cuspidate apex, cuneate base, 3 mm in width and 1 mm in length.

*Sepals*.—Fused with hypanthium.

*Petals*.—5, fused into a funnel form tube with apex and 5 lobes, corolla 1.5 cm in length, 4 mm in width at base, 10 mm in width near apex, tube portion 8 mm in length, free portions are 7 mm in length and 4 mm in width, shape of free portions is ovate with obtuse apex, inner surface glabrous, outside surface pilose, color on all surfaces 4B.

Reproductive organs:

*Gynoecium*.—1 pistil, an average of 2.2 cm in length, style 2 cm in length and 1A in color, stigma is about 1 mm in diameter and 138B in color, ovary is round in shape, 3 mm in length and diameter and 138A in color.

*Androecium*.—5 stamens, about 7 mm in length, adnate to inner surface of corolla tube, filaments are 2C in color and about 4 mm in length, anthers are 2A in color, pollen is very abundant in quantity and 2A in color with 100% acetocarmine stain.

*Compatibility*.—Self-incompatible.

Fruit description:

*Fruit development*.—60 days from mid-bloom to harvest.

*Harvest date*.—Average of June $10^{th}$ in Corvallis, Oreg., fruit matures over several days and may require 3 harvests.

*Fruit type*.—True berry, consists of 2 ovaries enclosed in fleshy bracts.

*Fruit shape*.—Some are elliptical and some have rolled edges at apex appearing jug-shaped.

*Fruit size*.—An average of 2.4 cm in length and 1.5 cm in width.

*Fruit surface*.—Smooth with heavy bloom.

*Fruit apex*.—Flattened with an indent in the center.

*Fruit skin color*.—103B with bloom removed, 98C with bloom.

*Fruit flesh color*.—143B.

*Fruit firmness*.—Medium firm.

*Fruit brix*.—14°.

*Fruit juiciness*.—Low.

*Fruit taste*.—Sweet.

*Fruit weight*.—An average of 2.2 gm.

*Peduncle*.—4 to 5 mm in length.

*Pedicel-berry scar*.—Very small, dry.

*Fruit attachment strength*.—Medium; strong enough to avoid pre-harvest drop and loose enough to pick without tearing berry flesh.

*Post-harvest*.—Berries maintain their appearance, firmness and taste for at least 2 weeks in cold storage at 33° F. to 35° F.

*Fruit yield*.—Above average for a Japanese haskap, 2.1 kg on a 6 year-old plant.

*Market uses*.—Fresh and frozen fruit and particularly suited for processed products.

*Seed*.—Average of 8 seeds per fruit, dried seeds; lenticular in shape, dry weight size is 142 mg/100 seeds, N199D in color.

It is claimed:

1. A new and distinct cultivar of Japanese haskap plant named 'Pirika' as herein illustrated and described.

* * * * *